United States Patent [19]

Hai et al.

[11] Patent Number: 6,018,035
[45] Date of Patent: Jan. 25, 2000

[54] REAGENTS FOR ISOTROPIC SIZE ENHANCEMENT OF A PEPTIDE, PROTEIN, NUCLEOTIDE OR OTHER SUBSTRATE

[75] Inventors: Ton That Hai, Mundelein; David E. Pereira, Crystal Lake; Deanna J. Nelson, Libertyville, all of Ill.

[73] Assignee: Baxter International Inc., Deerfield, Ill.

[21] Appl. No.: 08/897,336

[22] Filed: Jul. 21, 1997

[51] Int. Cl.$^7$ .......................... C07H 19/00; A61K 31/70
[52] U.S. Cl. ........................ 536/22.1; 536/1.11; 536/4.1; 536/17.2; 536/18.7; 536/20; 536/21; 536/51; 536/53; 536/112; 536/123.1; 514/23; 514/25; 514/42; 514/54; 514/55; 514/56; 514/59
[58] Field of Search ..................... 536/1.11, 4.1, 536/17.2, 18.7, 20, 21, 22.1, 51, 53, 112, 123.1; 514/23, 25, 54, 55, 56, 59, 42

[56] References Cited

U.S. PATENT DOCUMENTS

| | | | |
|---|---|---|---|
| 4,613,665 | 9/1986 | Larm | 536/20 |
| 4,698,387 | 10/1987 | Schmidt et al. | 525/54.1 |
| 4,900,816 | 2/1990 | Wong | 536/120 |
| 4,943,630 | 7/1990 | Jacquinet et al. | 536/123 |
| 5,079,337 | 1/1992 | Leonard et al. | 530/385 |
| 5,110,909 | 5/1992 | Dellacherie et al. | 530/385 |
| 5,248,766 | 9/1993 | Nelson et al. | 530/785 |
| 5,510,418 | 4/1996 | Rhee et al. | 525/54.2 |
| 5,527,893 | 6/1996 | Burns et al. | 514/53 |
| 5,605,938 | 2/1997 | Roufu et al. | 514/59 |

FOREIGN PATENT DOCUMENTS

WO 96/34889  11/1996  WIPO .......................... C07K 14/805

OTHER PUBLICATIONS

Hascall et al., Immunology of Chondroitin/Dermatan Sulfate, in Glycoimmunology, Alavi, A. and Axford, A. S. eds., Plenum Press, New York, pp. 205–216 (1995)–published sufficiently before filing date such that the month is not an issue. month not available.

Connective Tissue Proteoglycans, in The Biochemistry of Glycoproteins and Proteogycans, W. J. Lennarz ed., Plenum Press, New York, pp. 286–314 (1980). month not available

*Primary Examiner*—Kathleen K. Fonda
*Attorney, Agent, or Firm*—Senniger, Powers, Leavitt & Roedel

[57] ABSTRACT

Novel polysaccharide compounds are disclosed for decorating biomolecular surfaces to increase isotropic size and mask antigenicity. The oligosaccharides may be synthesized as repeating disaccharide units, or may be derived by acid hydrolysis of naturally occurring polysaccharides. Such natural sources include chondroitins obtained from shark cartilage, or hyaluronic acid. The polyanionic sulfate groups contained in the sugar moieties impart negative charges which repel the molecules from the negatively charged wall of capillaries, to lengthen retention times of decorated drug molecules, such as crosslinked hemoglobin, in the peripheral circulation.

4 Claims, 8 Drawing Sheets

1. Linker No. 1

2. Linker No. 2

3. Branched Linker

REAGENTS FOR ISOTROPIC SIZE ENHANCEMENT OF A PEPTIDE, PROTEIN, NUCLEOTIDE OR OTHER SUBSTRATE

CROSS REFERENCE TO RELATED APPLICATION

This application hereby incorporates by reference the complete text of application Ser. No. 08/896,743, entitled "THERAPEUTIC HEMOGLOBIN COMPOSITION HAVING ISOTROPICALLY INCREASED SIZE", by inventors Ton That Hai, David E. Pereira and Deanna J. Nelson, filed on the same date as this application, Jul. 21, 1997.

FIELD OF THE INVENTION

This invention relates to reagents for isotropic size enhancement and surface modification of biopolymers. Polyanionic oligosaccharides covalently joined to a linker molecule with one or a plurality of activated free termini reactive with nucleophilic moieties on the surface of such biopolymers.

BACKGROUND OF THE INVENTION

It is well documented that therapeutic performance of exogenously administered proteins is compounded by problems of poor pharmacokinetics and pharmacodynamics, and immunogenicity when administered to humans. A short half-life in the systemic circulation resulting from rapid clearance from the blood, degradation by plasma proteases, or inactivation by specific inhibitors impairs efficacy. Repeated parenteral administration of a heterologous (non-host) protein generally results in an immunogenic response that accelerates the clearance of the protein from the blood. Such administration may also lead to the development of hypersensitivity. If a human-derived protein is produced by a cell other than the human cell in which it is normally expressed, it may lack the proper post-translational modifications, and may in its unmodified form be immunogenic. In these instances, severe allergic reactions are common and anaphylactic death may ensue.

There has been a number of attempts to covalently attach small molecules to peptides, proteins and other biosurfaces for the purpose of improving therapeutic performance. The theory is that conjugation with poorly immunogenic substrates would mask determinant sites on the protein surface responsible for immunogenicity. Moreover, the theory is that conjugates having increased size would be expected to exhibit lower clearance rates and corresponding extended circulating life following infusion. Likewise, conjugation of small molecules and polymers to antigenic surfaces would mask protein-absorption sites on the surface of a material, device, or instrument.

Polysaccharides such as dextran exemplify polymers that may be covalently attached to peptides, proteins or surfaces for the purpose of improving their therapeutic performance. A polysaccharide that is a reducing sugar contains an aldehyde group present as a hemiacetal. In its hemiacetal form the polysaccharide is too unreactive to be practical for surface modification. Also, the size of the polysaccharide interferes sterically with reaction at this site. In addition, if the polysaccharide is negatively charged, as is for example, dextran sulfate, the negative charges can effect electrostatic hindrance to their utility as surface modification reagents. For these reasons, polysaccharides are generally regarded as not useful for surface modification without additional modification to minimize or eliminate these shortcomings.

In general, conjugate-modified peptides and proteins exhibit properties which are different from those of the native protein. Conjugation has been used with varying degrees of success to alter certain physical characteristics of peptides and proteins, including size, stability, resistance to thermal or proteolytic inactivation, pH optimum, and solubility. Attachment of hydrophilic polymers to peptides or proteins has been used to enhance blood circulation half-life, alter the immunological response, protect against protease inactivation (or inappropriate protease activation), and enhance functional stability and increase solubility. However, proteins, whether native or molecularly modified, administered parenterally may also be antigenic, initiating undesirable immune responses. Repetitive administration of polymer-conjugated peptides or proteins may induce an immune response specific for the conjugated entity. Moreover, some modifications may inactivate some or all of the biological activity of the modified peptide or protein.

As an example of a protein with therapeutic utility, adenosine deaminase (ADA) catalyzes the irreversible deamination of adenosine to inosine. Inherent defects of ADA lead to abnormalities in purine nucleoside metabolism that are selectively toxic to lymphocytes and result in immune deficiency diseases. The native enzyme has limited therapeutic efficacy following its administration, because it is rapidly cleared from the systemic circulation. Adenosine deaminase has been subjected to a series of modifications in attempts to alter its clearance rate from the circulation. For example, modification of this enzyme with monomethyl polyethylene glycol (PEG) increased the circulating half-life in humans from minutes (native protein) to five days (MS Hershfield et al. *New England J Med,* 316: 589, 1987). However, immunological studies following repeated infusions demonstrated antibodies specific for the modified enzyme. (FF Davis et al. *Advances in Parenteral Sci Tech,* 4: 831–64, 1990)

Conjugation of small molecules or polymers to surfaces has altered the surface properties and performance characteristics thereof. The conjugating entity may enhance biocompatibility of the surface by weakening the interaction between plasma proteins and the surface, inhibiting deposition of undesired cells or macromolecules by altering the surface charge and the like. The net result of the enhanced biocompatibility is maintenance of functional performance and increased longevity of utility.

SUMMARY OF THE INVENTION

In design of therapeutic agents which circulate in the blood, it is highly desirable to be able to regulate the elimination rates, so that the optimal effect is achieved while an active form is still available to the target tissues. It is therefore an object of the present invention to provide molecular structures to modify therapeutic agents acting which are substrates for decoration. Such decorated substrates have altered properties of retention in the blood stream because isotropic enlargement prevents extravasation.

It is a further object to provide such molecular structures which lack immunogenicity (which can speed elimination of subsequently administered agent), and which can even mask potential immunogenic sites on the therapeutic agent's surfaces.

Polysaccharides contained in tissue such as cartilage are known to be, and must be, of low antigenicity since they are ubiquitous in the animal kingdom and perform similar functions from species to species. These polysaccharides may be broken down into oligosaccharides of repeating sugar units, and the reducing end may be modified chemically to react with groups capable of attaching to the surface of therapeutic agents. It is desirable also to include a linker, also of benign immunogenicity (e.g. of low antigenicity or not immunogenic in the species to which it is administered), to prevent steric hindrance between the reactive group on the oligosaccharide linker molecule and a nucleophilic group on the substrate therapeutic agent surface.

In accordance with the present invention, compounds are provided with the following formula I:

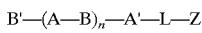

wherein A and B are sugars which may be of N-acetylgalactosamine, N-acetylglucosamine, glucuronic acid, iduronic acid or glucose forming a repeating disaccharide unit in which A and B are joined covalently by a glycosidic bond between C-1 of sugar A and C-3 or C-4 of sugar B. The A–B disaccharide units are joined covalently to form an oligosaccharide by a glycosidic bond between C-1 of penultimate sugar B of a first disaccharide unit and C-3 or C-4 of sugar A in the next successive disaccharide unit. B' is a sugar at the non-reducing terminus of the oligosaccharide of ring structure identical to sugar B, and A' is a 1-amino, 1-amido, or 1-imino acyclic hexose joined covalently by a glycosidic bond between C-1 of sugar B at the terminus opposite the non-reducing terminus of said oligosaccharide and C-3 or C-4 of sugar A'. This structure is further joined covalently at the 1-amino, 1-amido, or 1-imino linkage to linker L comprising an aliphatic, acyclic carbon chain containing one or more moieties, which can be an ether, thio ether, or amide. The linker bridges sugar A' and one or more electrophilic groups Z, which may be an aldehyde, an activated ester of a carboxylic acid, a maleimide, an epoxide, a tosyl or tresyl ester, or a halide.

The foregoing compounds are constructed from oligosaccharides which may be derived from chondroitin-4-sulfate, chondroitin-6-sulfate or hyaluronic acid. "Derived" herein means hydrolyzing these native polysaccharide by acid hydrolysis, down to oligosaccharides of a molecule size range of 1,000 to 15,000 Daltons.

DETAILED DESCRIPTION OF THE PREFERRED EMBODIMENT

Figure 1:
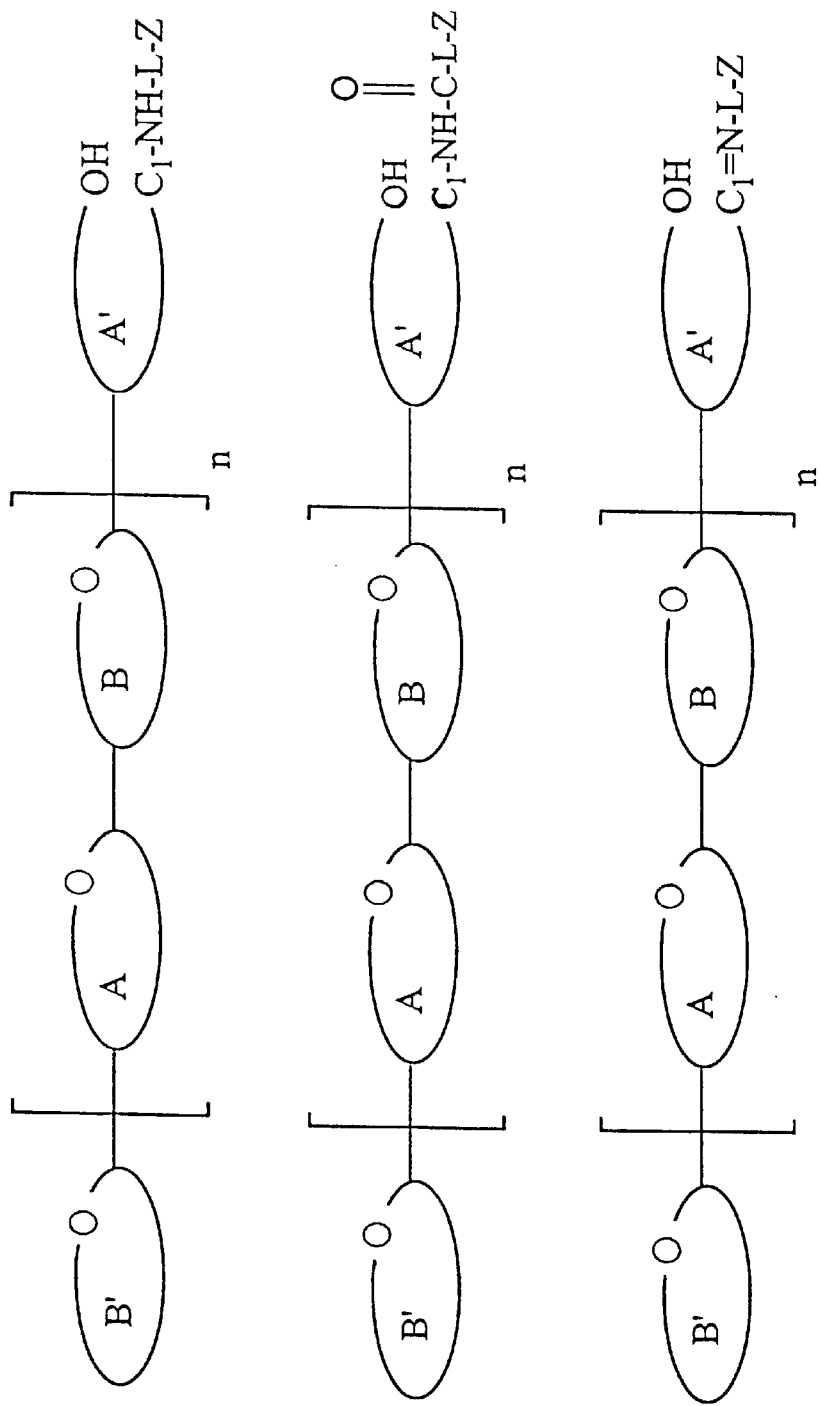
FIG. 1 gives a schematic structure for disclosed compounds showing the configuration of the modified sugar A' at the reducing termini of the amino, amido, and imino forms.

In Formula I and FIG. 1, each ring structure A, A', B and B' is a sugar. Each sugar contains at least one substituent selected from the group consisting of —$CO_2^-$, —$OSO_3^-$, —$NHCOCH_3$, and —$NHSO_3^-$. The remaining substituents on the sugar ring are selected from the group consisting of —H, glycosidic —O— and —OH. The repeating unit of the oligosaccharide comprises sugar A and sugar B, wherein sugar A is covalently joined to sugar B by a glycosidic bond from carbon-1 of sugar A to carbon-3 or carbon-4 of sugar B, wherein sugar B is covalently joined to sugar A by a glycosidic bond from carbon-1 of sugar B to carbon-3 or carbon-4 of sugar A, and n is an integer from 2 to about 20. Sugar B', which is positioned at the non-reducing terminus of the oligosaccharide has a structure identical to that of sugar B, with the exception that it is not covalently joined by a glycosidic bond at carbon-3 or carbon-4 to any other sugar. Sugar A', the erstwhile reducing sugar of the oligosaccharide, has a structure identical to that of sugar A, with the exception that the latent aldehyde that was present at carbon-1 of the sugar has been modified by reductive amination or imination to enable covalent joining to one terminus of a linker L.

The sugars A, A', B, and B' which are useful in the present invention may be commonly named as, for example, N-acetylglucosamine, glucuronic acid, N-acetylgalactosamine, iduronic acid, and glucose.

Linker L is an organic bridge having a length of from about 10 Å to about 300 Å and having a plurality of termini, one of which is covalently joined as an amine or imine to carbon-1 of sugar A' and each of the remainder of which terminates as and is covalently joined to Z, an organic functionality which provides a reaction group for covalent coupling to a nucleophile.

The organic bridge of linker L may be an acyclic, aliphatic carbon chain containing ether, thioether, or amide moieties and has a linear portion extending from sugar A' and a linear or branched portion that incorporates the remaining terminus or termini.

Figure 2:
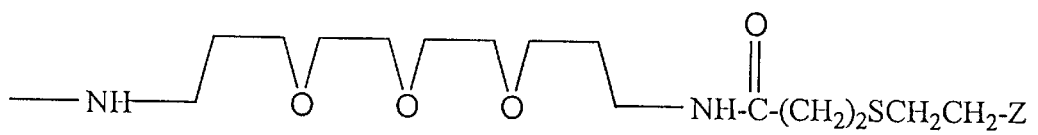
FIG. 2 shows molecular formulas for three suitable linkers.
Figure 2:
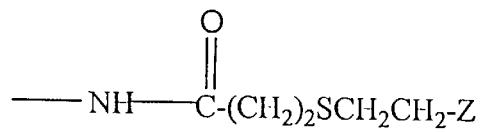
Figure 2:
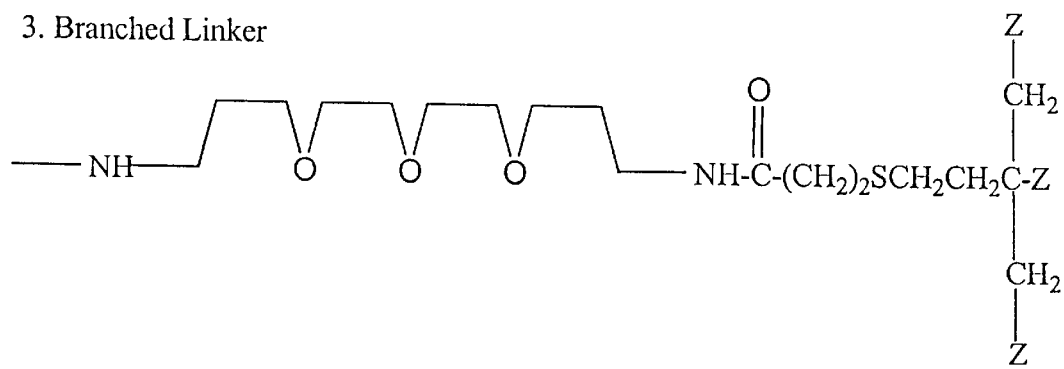

The purpose of the linker is to position the reactive group away from the oligosaccharide chain so as to avoid steric hinderance of the coupling reaction forming the conjugated macromolecule. It is important that the linker be aliphatic and acyclic with an absence of double bonds or aromatic rings. The incorporation of ethylene or diethylene glycol moieties, amide bonds, and thioether groups reduces antigenicity and provides for water solubility. The linker may contain one or more of these moieties as illustrated in the structures set forth in FIG. 2. The linker may be completely linear or may be branched at the terminus opposite its point of covalent attachment to sugar A'. The branched termini may each end in a Z group, to create a plurality of attachment points between the macromolecular surface and the oligosaccharide strand.

Figure 4A:
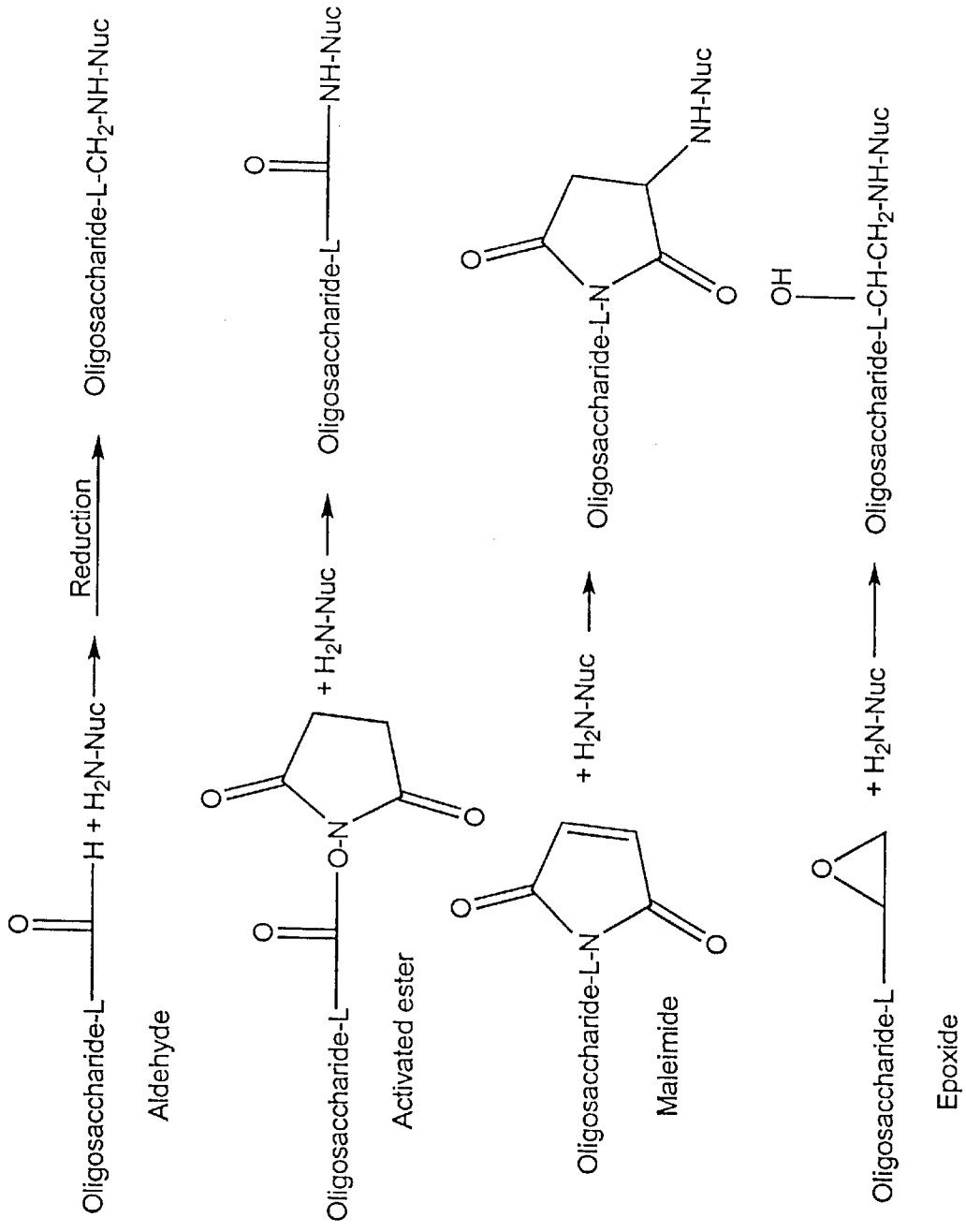
FIG. 4 gives the molecular structures for a number of possible Z groups useful in the disclosed compounds.
Figure 4B:
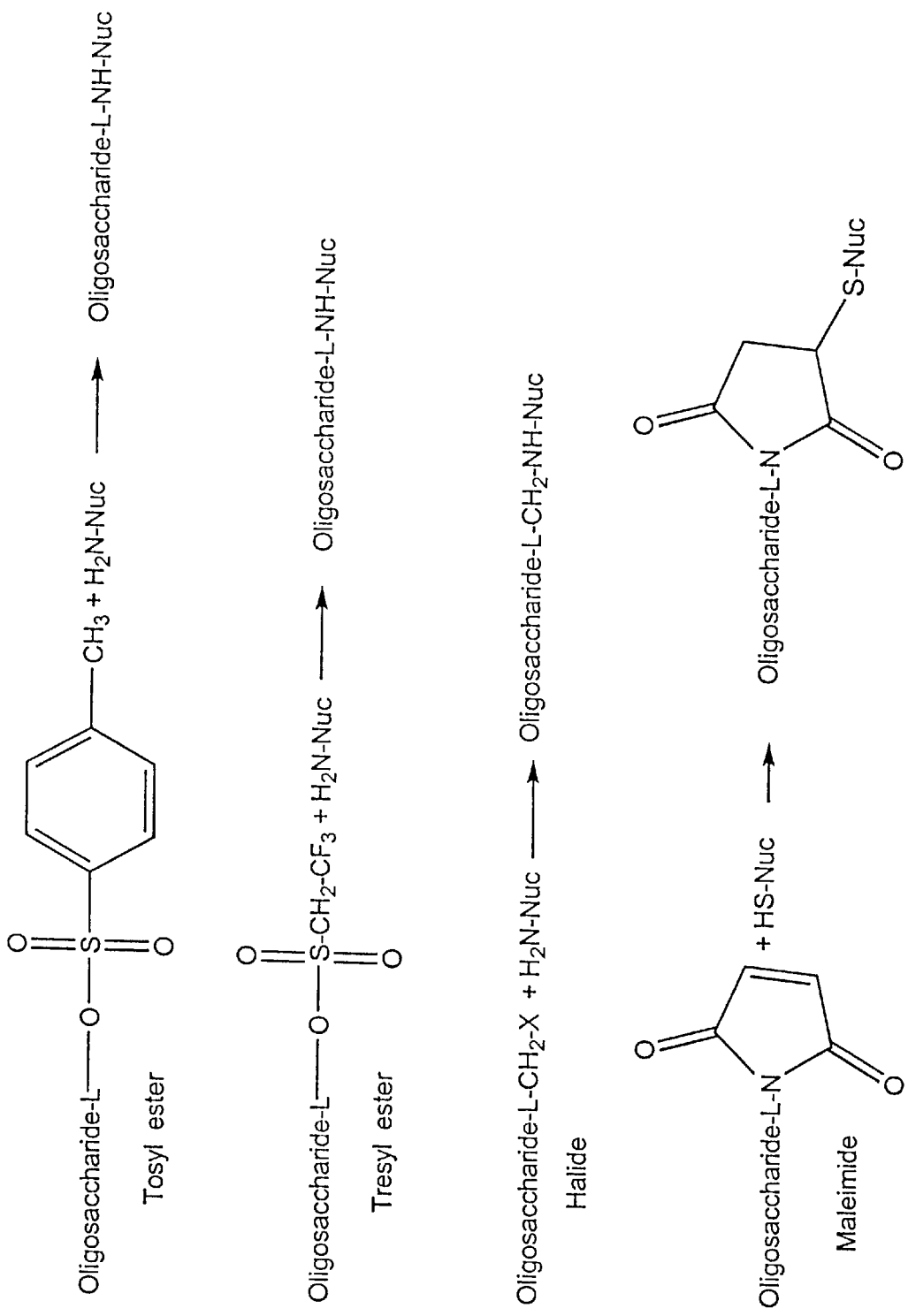
Figure 4C:
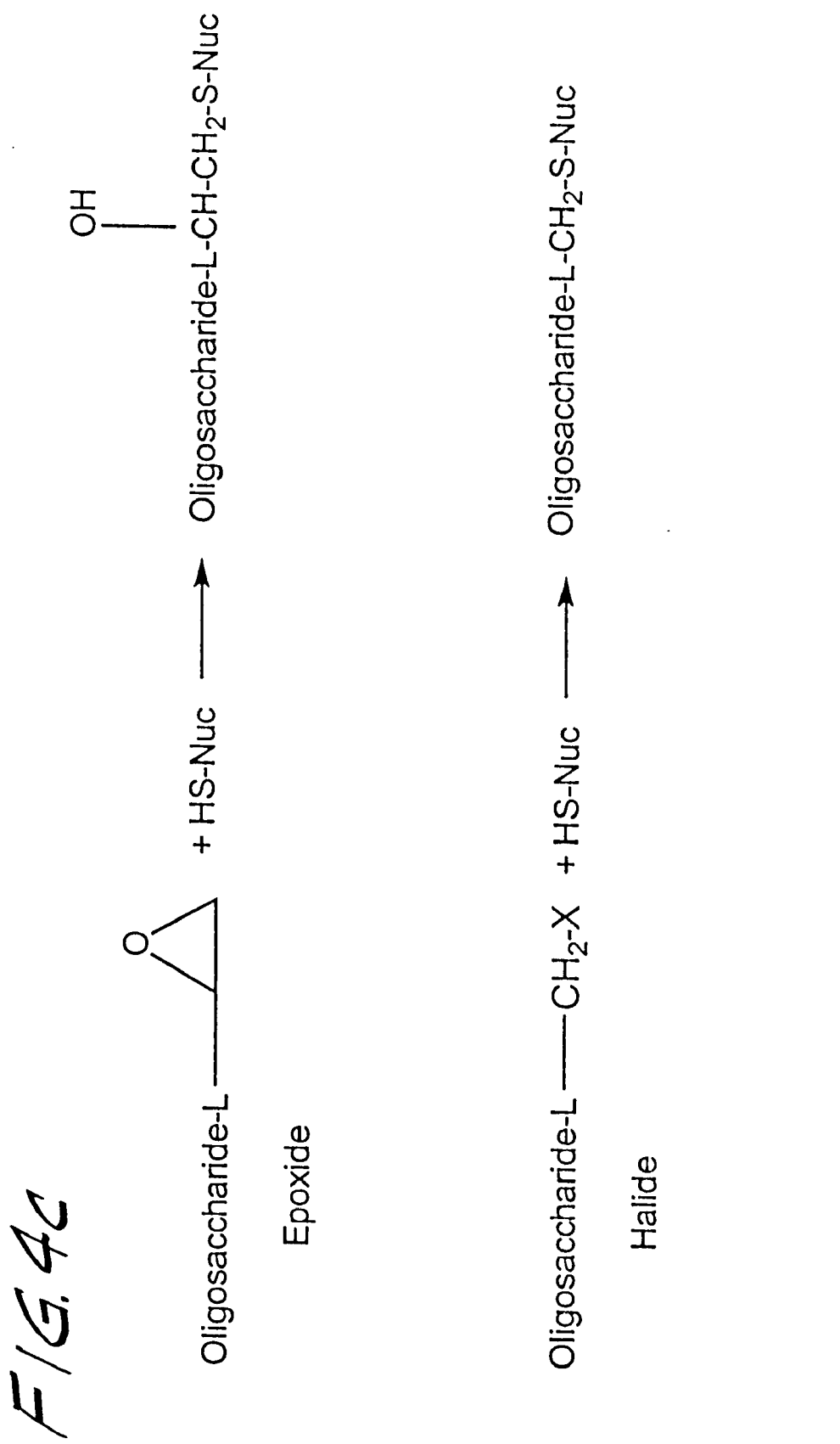

An organic functionality Z is covalently joined to each free terminus of linker L joined to sugar A' as shown in FIG. 1. Functionality Z will react with a nucleophile to form a covalent bond between a reagent of the present invention and the nucleophile. For example, if Z is an aldehyde, an activated ester of a carboxylic acid, a maleimide, an epoxide, a tosyl or tresyl ester, or a halide, such a reagent of the present invention will react with an amine nucleophile to yield a product in which the said reagent is covalently joined to an amine nucleophile as an imine or amine (after reduction), an amide, an amine-substituted maleimide, a beta-hydroxy amine, or an amine, respectively (see FIG. 4 for typical reactives). A Z halide, maleimide, or epoxide, will also react with a sulfhydryl nucleophile to yield a product covalently joined to the sulfhydryl nucleophile as a sulfide, a thio-substituted maleimide, or a beta-hydroxy sulfide, respectively.

Many examples of these chemistries are given in *Chemistry of Protein Conjugation and Cross-linking,* S. Wong, CRC Press, Inc. (1991) which is incorporated by reference herein.

The molecular weight of the reagent of Formula I is from about 1,000 to about 15,000 Daltons, more preferably from about 1,000 to about 10,000 Daltons, and most preferably about 5,000 Daltons. The oligosaccharide component of Formula I may be synthesized de novo or may be derived from natural sources. In a preferred embodiment, the oligosaccharide is a hydrolysate of chondroitin sulfate. The hydrolysis is carried out conventionally, and the fragments may be sorted by known sizing methods to produce a population of desired length having less than five percent contamination by oligosaccharides of a length different from the desired length.

Substrates suitable for modification by the present reagents include peptides, proteins, nucleotides, polynucleotides, pharmaceutic agents, diagnostic agents, and polymers which have at least one nucleophilic functional group capable of forming a covalent bond with the terminus of the linker. One substrate of interest is diaspirin crosslinked hemoglobin (DCLHb) described in U.S. Pat. Nos. 4,598,064, 4,600,531, RE 34,271.

Figure 3A:
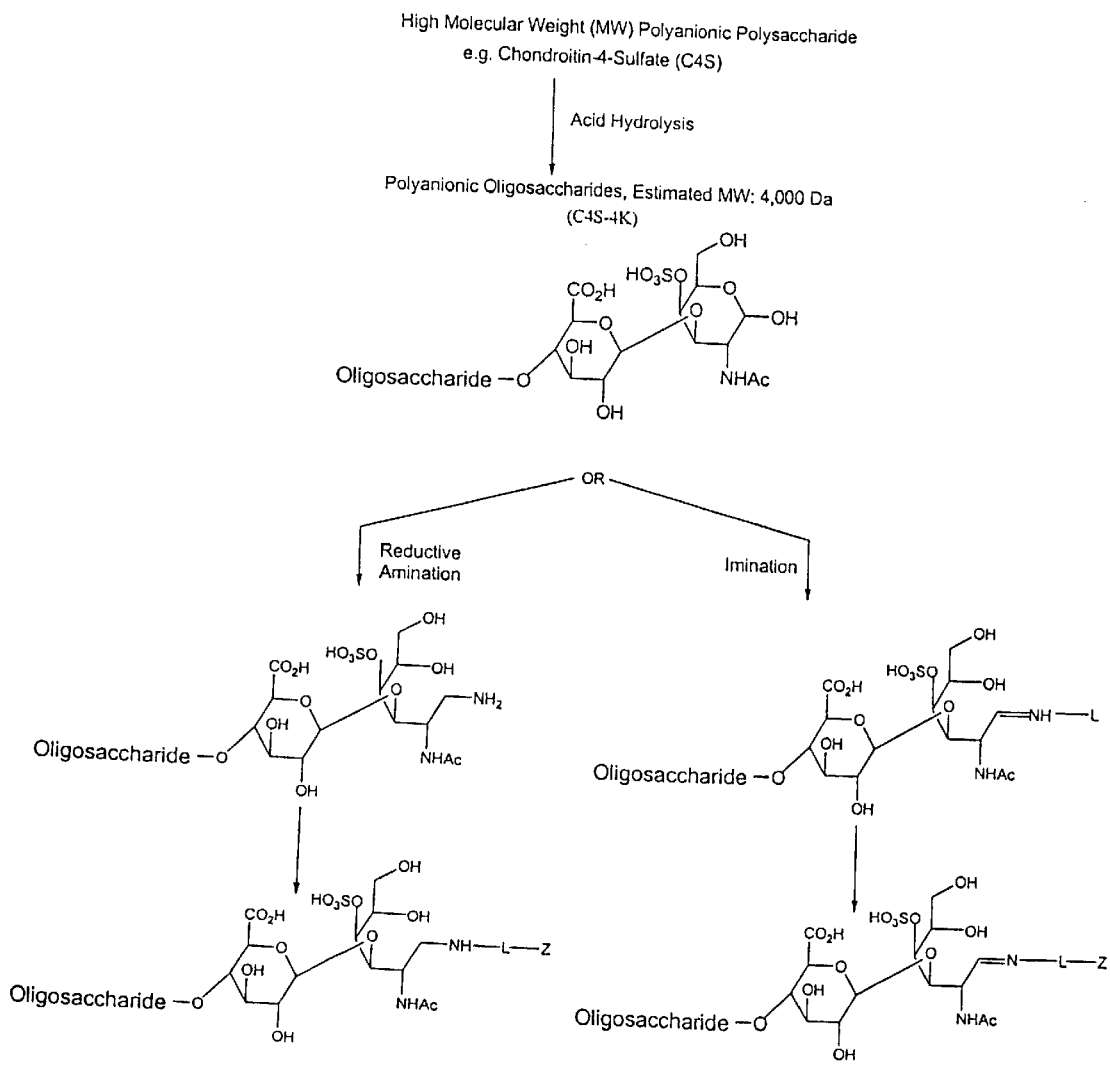
FIGS. 3a, 3b and 3c show the chemistries of the reducing end moieties starting with three different native polysaccharides.
Figure 3B:
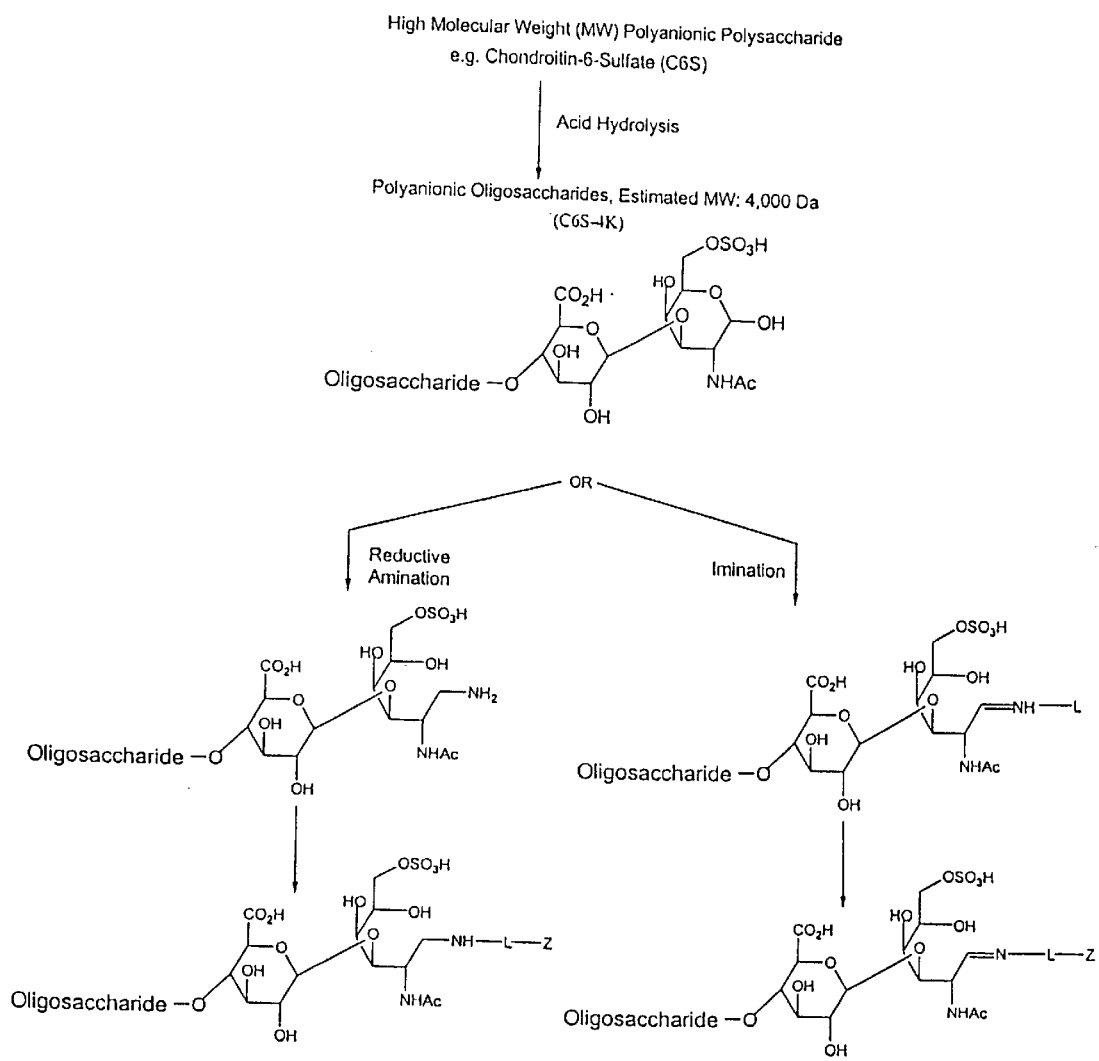
Figure 3C:
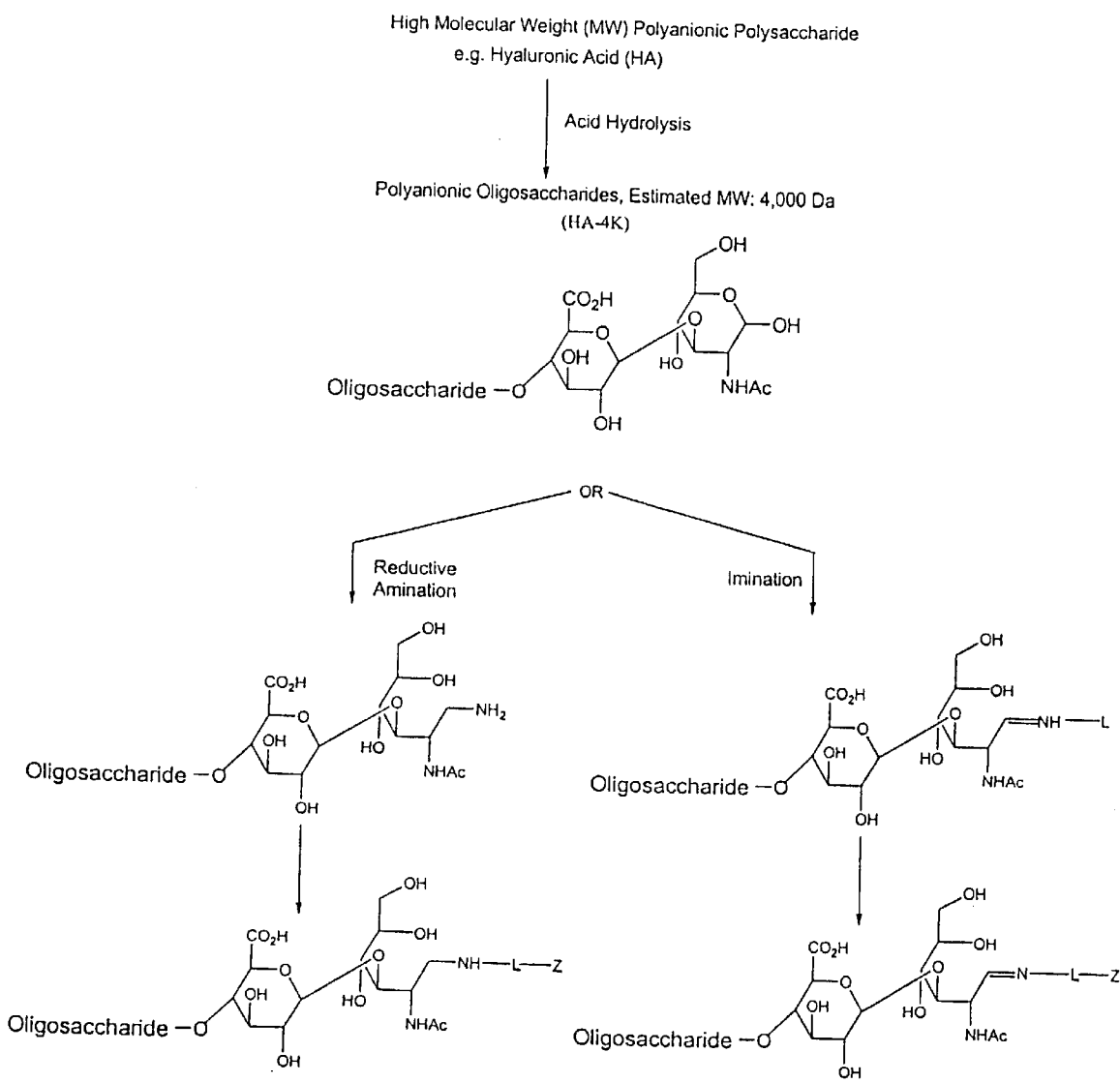

FIGS. 3a–c are flow diagrams showing structures of compounds provided in the reaction pathway in the synthesis of three reagent compounds. In FIG. 3a the starting material is an acid hydrolysate (polyanionic oligosaccharides) derived from chondroitin-4-sulfate. The terminal sulfate sugar is converted by reductive amination or imination to the structures shown, and then further reacted with the linker moiety containing a Z reaction group. Z reaction groups comprise an aldehyde, activated ester of a carboxylic acid, maleimide, tosyl ester, tresyl ester, halide, or epoxide. As depicted in the equation shown in FIG. 4, the Z group reacts with either an amino nucleophile or sulfhydryl nucleophile to form a bond covalently coupling the oligosaccharide linker moiety to the protein or other macromolecule.

The polyanionic oligosaccharide portion of the reagents is selected to mimic the structure and properties of glycosaminoglycans found naturally in the extracellular matrix. Thus, the polyanionic oligosaccharides are linear sugars, have a non-reducing terminus and a terminus opposite the non-reducing terminus, and are constructed from a repeating disaccharide unit. The two sugars of the disaccharide unit are joined covalently by a glycosidic bond between C-1 of one sugar and C-3 or C-4 of a second sugar and each sugar of each repeating disaccharide unit is joined covalently by a glycosidic bond to another sugar.

The oligosaccharide portion of the reagents may be obtained by acid or enzyme catalyzed hydrolysis of natural polysaccharides or may be synthesized de novo. For example, the polyanionic polysaccharides chondroitin 6-sulfate, chondroitin-4-sulfate or hyaluronic acid may be hydrolyzed with acid catalysis to a mixture of polyanionic oligosaccharides and the fragments may be sorted by known sizing methods to produce a population of desired length. In the case of chondroitin-6-sulfate the repeating disaccharide is N-acetylgalactosamine-6-sulfate joined covalently by a glycosidic bond to glucuronic acid.

In the case of chondroitin-4-sulfate the repeating disaccharide is N-acetylgalactosamine-4-sulfate joined covalently by a glycosidic bond to glucuronic acid. In the case of hyaluronic acid the repeating disaccharide is N-acetylglucosamine joined covalently by a glycosidic bond to glucuronic acid.

Likewise, starch may be hydrolyzed with acid or enzyme catalysis to a mixture of oligosaccharides and the fragments may be sorted by known sizing methods to produce a population of desired length. The selected population of fragments may be sulfated by conventional means to produce a polyanionic oligosaccharide having repeating disaccharide units comprised of glucose and sulfated glucose joined covalently by glycosidic bonds.

FIGS. 3b and 3c show the reaction and compounds formed where the starting materials are acid hydrolyzed chondroitin-6-sulfate and hyaluronic acid, respectively. In each case, a linker has a Z reaction group at its non-sugar terminus.

It as an object of the present invention to provide a reagent which couples relatively nonimmunogenic carbohydrate species to the surface of macromolecules such as proteins. Typically the antigenic determinant of such macromolecules resides at the surface and contains reactive water solubilizing groups such as —$NH_2$ or —COOH. Thus, targeted reactions coupling the substantially nonimmunogenic oligosaccharides at —$NH_2$ increase the probability that an antigenic epitope will be camouflaged by the oligosaccharide.

The reagents of the present invention can be useful for conjugation to surfaces for the purpose of altering certain physical characteristics of the surfaces. Thus, conjugation of said reagents to peptides and proteins has been shown to alter their physical characteristics, such as size, stability, resistance to thermal or proteolytic inactivation, pH optimum, and solubility. In addition, attachment of the reagents to peptides or proteins extends blood circulation half-life, reduces or obviates antigenicity, protects against protease inactivation (or inappropriate protease activation), and may enhance stability. In addition, relatively insoluble peptides can show enhanced solubility. Similarly, the reagents of the present invention can be used to treat surfaces to inhibit blood clotting or coagulation at the surface, to suppress plasma protein adhesion or binding to surfaces, or to prevent protease or other enzyme degradation interfering with functional performance of the surface.

A simple in vitro test may be used for assessing the effect of chemical modification of proteins by the present reagents in masking surface structure as measured by red cell or platelet aggregation. In this test, human blood is diluted with a physiological electrolyte solution (negative control) or is diluted proportionally with combinations of modified protein and physiological electrolyte solution (test solutions) and then incubated. A slide of each solution is prepared. If there is no interaction between the test sample and red cells or platelets, the red cells are dispersed randomly throughout the sample. However, if there is interaction between the test sample and red cells or platelets, aggregates of red cells and platelet "clumps" are observed. The extent of aggregation is correlated with the concentration of modified protein in the test solution and scored on a scale from zero to three. A score of zero indicates that no aggregation was observed; a score of three indicates that extensive aggregation was observed that could not be reversed by the addition of normal saline solution. These scores correlate with in vivo biocompatibility, in that when aggregation is observed in the in vitro test, there is a trend for more rapid oxidation to methemoglobin, for example, aggregate formation and more rapid clearance following infusion in vivo. Thus, proteins modified by decoration with the present reagents score less than two in this test, and even the most antigenic score zero or one.

The utility of a reagent may be demonstrated by comparing the extent of protein absorption to the surface prior to conjugation with a reagent with that observed after modification. Alternatively, the utility of a reagent may be demonstrated by comparing the longevity of functional utility of a surface that is not modified with that of a reagent-modified surface.

The following examples describe specific embodiments of the present invention. Example 1 discloses methods by which the oligosaccharide component of the present reagents may be obtained. Example 2 presents methods by which an oligosaccharide component may be reductively aminated or iminated to yield an oligosaccharide linker conjugate. Finally, Example 3 discloses the preferred methods by which a Z functional group is covalently joined to an oligosaccharide-L component to yield composite reagents.

EXAMPLE 1. PREPARATION OF REPRESENTATIVE OLIGOSACCHARIDES

In the examples, two chromatographic methods were used to monitor reactions and to characterize the products. Size-exclusion chromatography (SEC) was performed using Superdex™ 200 column (Pharmacia), a mobile phase consisting of 50 mM phosphate, pH 7.0, containing 0.15 M NaCl, delivered at a flow rate of 0.7 mL/min., and analyte detection at 214 nm for oligosaccharide reagents and at 280 nm for modified peptide or protein. In this assay, materials elute from the stationary phase in the order from largest to smallest in size, i.e., larger entities elute with shorter retention times and smaller entities elute with longer retention times. Reversed-phase high performance liquid chromatography (RP-HPLC) was performed using a Vydac Protein C-4 column, with elution using mobile phases (A) and (B) delivered at 1 mL/min. as a linear gradient having the following compositions over time: 1) 50% B to 55% B over 20 minutes; 2) 55% B to 75% B over 10 minutes; 3) 75% B to 85% B over 10 minutes. Mobile phase (A) consisted of $CH_3CN/H_2O/TFA$, 20:80:0.1, by volume. Mobile phase (B) consisted of $CH_3CN/H_2O/TFA$, 60:40:0.1, by volume. Analytes were monitored at 280 nm.

A. Preparation of a representative oligosaccharide from chondroitin-4-sulfate. Chondroitin-4-sulfate (400.8 g) was dissolved in 5 L of 0.5 N HCl. The solution was heated to 65° C. for about 24 hours and then cooled to ambient temperatures using an external ice bath. The solution pH was adjusted to 7.6 by the addition of 5 N NaOH. To the solution was added 12 L of ethanol. An oily precipitate formed. The solvent was decanted, and 4 L of ethanol was added. The mixture was stirred to obtain a granular solid. The solid was collected by filtration and washed successively with ethanol (2×500 mL) and ethyl ether (1×500 mL). The solid was dried under vacuum to give 343.5 g of product having an SEC retention time of about 27 minutes. This material was identified by the acronym "C4S-4K".

B. Preparation of a representative oligosaccharide from chondroitin-6-sulfate. Chondroitin sulfate, Type C (18.4 g; from shark cartilage, reported molecular weight of 25–50 kiloDaltons; Maruha Corporation) was dissolved in 0.5 N HCl (230 mL), and the stirred solution was heated at 65° C. for 24 hours. The reaction mixture was cooled to room temperature, and then the solution pH was adjusted to pH 7.4 with 5 N NaOH (25 mL). The stirred solution was slowly diluted with ethanol (600 mL) and then maintained at 5° C. for three hours before the supernatant was removed by decantation. The oily residue was stirred with ethanol (200 mL) for 10 minutes and the supernatant was discarded. The residue was stirred vigorously with ethanol (400 mL) to precipitate the product, which was collected by filtration, washed successively with ethanol and ethyl ether and dried under high vacuum. The product (18.12 g) has a SEC profile characterized by a peak having a retention time (at the peak maximum) of about 27 minutes. This material was identified by the acronym "C6S-4K".

C. Preparation of a representative oligosaccharide from hyaluronic acid. A viscous slurry of hyaluronic acid (18.4 g, Bioiberica) in 0.5 N HCl (300 mL) was stirred vigorously at 65° C. The reaction was monitored by SEC. After heating at 65° C. for 19 hours, the reaction mixture was cooled to room temperature, and the solution pH was adjusted to 7.4 with 5 N NaOH (29 mL). The solution was filtered through $0.45\mu$ pore-size filter membrane, and the filtrate volume was reduced to 180 mL by evaporation under high vacuum. The solution was stirred during slow dilution with ethanol (750 mL) to give an oily product. After discarding the supernatant, the oily product was stirred with fresh ethanol (300 mL) to give a granular solid (14 g), which was collected by filtration, washed with ethanol and then ethyl ether, and dried under high vacuum. The product was characterized by an SEC retention time (peak maximum) of 26 minutes. This material was identified by the acronym "HA-4K".

EXAMPLE 2. REDUCTIVE AMINATION OF REPRESENTATIVE OLIGOSACCHARIDES

A. Preparation of C4S-4K-DGBE. The reagent, diethylene glycol bis(3-aminopropyl)ether mono-t-butyl carbonate (DGBE-BOC) was prepared by known methods from diethylene glycol bis(3-aminopropyl)ether (DGBE) and di-t-butyl carbonate.

C4S-4K (222.0 g, 55.0 mmol) and DGBE-BOC (150.1 g, 470.5 mmol) were dissolved in 1.2 L of Sterile Water for Irrigation, USP, and the pH of the solution was adjusted to 8.31 by the addition of 1.00 N HCl. Ethanol (600 mL) was added to clarify the solution. Borane-pyridine complex (8 M, 57 mL) was added to the solution. The reaction was monitored by TLC (silica gel; eluent: 2-propanol:$NH_4OH$:$H_2O$, 6:1:3, by volume; detection by exposure to 2,3,5-triphenyltetrazolium chloride). The solution was heated at 40° C. for four days and then cooled to ambient temperatures. The solution pH was adjusted to 10.03 by the addition of 5.00 and 1.00 N NaOH. Ethanol (12 L) was added, and the resulting slurry was stirred for three hours. The precipitate was allowed to settle for about one hour, the solvent was decanted, and the solid was collected by filtration and washed successively with ethanol (2×500 mL) and ethyl ether (1×500 mL). The solid was dried under vacuum to constant weight (210.7 g). This material was identified by the acronym "C4S-4K-DGBE-BOC". Removal of the BOC group was achieved by treatment of C4S-4K-DGBE-BOC with fifteen equivalents of HCl in water at pH 0.8 for 24 hours to afford the desired product, which was identified by the acronym "C4S-4K-DGBE".

B. Preparation of C6S-4K-DGBE. A solution of C6S-4K (17 g, 4.25 mmol) and BOC-DGBE (13.62 g, 42.5 mmol) in deionized water (85 mL) was adjusted to pH 8.4 with 1 N HCl (38 mL). Borane-pyridine complex (8 M, 42.5 mmol, 5.31 mL) and ethanol (30 mL) were added successively, and the clear solution was stirred at 40° C. The reaction was monitored by TLC (silica gel; eluent: 2-propanol:$NH_4OH$:$H_2O$, 6:1:3, by volume; detection by exposure to 2,3,5-triphenyltetrazolium chloride). After four days, the reaction mixture was cooled to room temperature, and the solution pH was adjusted to 10.0 with 1 N NaOH (22 mL). Water (25 mL) was added, and the solution slowly was diluted with ethanol (1 L) to precipitate the product, which was identified by the acronym "C6S-4K-DGBE-BOC". The latter (15.8 g) was collected by filtration, washed successively with ethanol and ethyl ether and dried under high vacuum. Dilute (1 N) HCl (52.2 mL) was added to a solution of C6S-4K-DGBE-BOC (13.9 g) in water (50 mL) to give a solution having a pH of 0.80. After stirring at room temperature for 24 hours, the solution was evaporated to dryness. The residue was dried under high vacuum to give solidified product (13.2 g), which was identified by the acronym "C6S-4K-DGBE".

C. Preparation of HA-4K-DGBE. HA-4K (10.0 g, 2.5 mmol) and BOC-DGBE (7.3 g, 23.8 mmol) were combined in 50 mL of water. The pH was adjusted to 8.25 with 1.00 N HCl. Borane-pyridine complex (8 M, 3.0 mL) was added, followed by 25 mL of ethanol. The solution was heated at 40° C. for five days. The solution was cooled to ambient temperature, and the pH was adjusted to 10.00 with 1.00 N NaOH. To the solution was added 500 mL of ethanol. The solid was collected after stirring for two hours. The solid was washed with ethanol (50 mL) and then with 100 mL of ethyl ether. The solid was dried under reduced pressure to give 9.5 g of the desired product, which was identified by the acronym "HA-4K-DGBE-BOC". An 8.5 g portion of this BOC-derivative was dissolved in 35 mL of water, and 35 mL of 1.00 N HCl was added. The pH of the solution was 0.85. The solution was stirred at room temperature for about 24 hours and then concentrated under vacuum to a volume of about 100 mL. Ethanol (800 mL) was added. The mixture was stirred, and after about 1.5 hours the solid was collected and washed with ethyl ether (25 mL). The solid was dried under reduced pressure to give 6.3 g of the desired product, which was identified by the acronym "HA-4K-DGBE".

D. Preparation of C4S-4K-$NH_2$. Borane-pyridine complex (4.7 mL, 8 M, 37.5 mmol) and ethanol (50 mL) were added to a solution of C4S-4K (15 g, 3.75 mmol) and an ammonium salt (168.75 mmol) such as ammonium acetate, ammonium bicarbonate, ammonium carbonate, ammonium carbamate or ammonium formate, for example, in water (100 mL). The solution was stirred and heated at 40–50° C. for four days. Analysis of the product mixture by TLC showed that the product mixture was negative to 2,3,5-triphenyltetrazolium chloride (a reagent for the detection of reducing sugars) and positive to ninhydrin. Then the reaction mixture was concentrated under vacuum to dryness and the residue was successively treated with water (100 mL) and concentrated under vacuum to dryness (3 times) to remove excess ammonium salt. The residue was dissolved in water (150 mL) and the solution was diluted with ethanol (600 mL) to give an oily product which was isolated by decantation. The oily product was stirred with ethanol (400 mL) to solidify the product, which was isolated by filtration, washed with ethyl ether, and dried under vacuum to constant weight (13.5 g). This material was identified by the acronym "C4S-4K-$NH_2$".

E. Preparation of C6S-4K-$NH_2$. It is chemically reasonable to predict that treatment of C6S-4K with an ammonium salt in the presence of a reducing agent such as borane-pyridine in the manner described above will yield the amine "C6S-4K-$NH_2$".

F. Preparation of HA-4K-$NH_2$. Borane-pyridine complex (BP; 2.12 mL; 8 M; molar ratio of BP/HA-4K of 10) and ethanol (25 mL) were added to a solution of HA-4K (6.8 g; 1.7 mmol; assumed MW of 4000) and ammonium carbonate (7.35 g, 76.5 mmol) in water (60 mL). The solution was stirred at 40° C. for five days and evaporated to dryness. The residue was dissolved in water (50 mL), and the solution was extracted with chloroform (3×50 mL) to remove excess borane-pyridine. The aqueous solution was concentrated under vacuum to dryness, and the residue was treated with water (4×50 mL) and reconcentrated to dryness to remove residual ammonium carbonate. The resulting residue was dissolved in water (50 mL), the solution was filtered through 0.45$\mu$ pore-size filter membrane, and the filtrate was diluted with ethanol (250 mL) to give an oily product. The supernatant was removed by decantation. The oily product was stirred with ethanol to give a solid (5.8 g), which was collected by filtration, washed successively with ethanol and ethyl ether and dried under high vacuum. This material was identified by the acronym "HA-4K-$NH_2$".

EXAMPLE 3. PREPARATION OF REPRESENTATIVE REAGENTS OF THE INSTANT INVENTION

A. Synthesis of the Aldehyde Derivative C4S-4-K-DGBE-TPA. N-Succinimidyl-4-thia-7-diethoxyheptanoate was prepared from 4-thia-7-diethoxyheptanoic acid using known methods. 4-Thia-7-diethoxyheptanoic acid was prepared by the condensation of methyl 3-mercaptopropionate (120.0 g, 1.0 mol) with 3-chloropropionaldehyde diethyl acetal in the presence of potassium carbonate (250.0 g, 1.8 mol) in 1 L of DMF and base-catalyzed hydrolysis of the ester using known methods.

C4S-4K-DGBE (140.0 g, 35.0 mmol) was dissolved in 1.2 L of water. The pH of the solution was adjusted to 9.10 with 5.00 NaOH. N-Succinimidyl 4-thia-7-diethoxyheptanoate (58.8 g, 170.0 mmol) in 500 mL of DMF was added dropwise. After the addition was complete, the solution was stirred four hours at ambient temperatures. The volume of solvent was reduced to about 500 mL by rotary evaporation. Ethanol (4 L) was added to the residual concentrate. The solution was decanted. Ethanol (4 L) was added and the mixture was kept at 5° C. The solvent was decanted. The resulting mixture was centrifuged to give a gel-like pellet. The pellet was diluted with acetone and evaporated to a semi-solid. Ethyl ether was added and the mixture was allowed to stand for one hour. The mixture was filtered and the gel-like solid was dried under vacuum at ambient temperatures. The solid was collected to give 104.7 g of product, an acetal which was identified by the acronym "C4S-4K-DGBE-TPDA".

C4S-4K-DGBE-TPDA (104.3 g) was dissolved in 750 mL of sterile water and 750 mL of 1.00 N HCl. The pH of the solution was adjusted to 2.00 with 1.00 N HCl. The solution was stirred for 3.5 hours. The reaction solution was concentrated under vacuum to a volume of about 100 mL. Acetone (250 mL) was added to precipitate the product as an oil. The solvent was decanted and an additional 250 mL of acetone was added. The mixture was agitated and the solvent was decanted. To the resulting semi-solid was added an additional 250 mL of acetone. The mixture was allowed to stand for one hour. The resulting solid was collected and washed with 100 mL of acetone. The solid was dried under vacuum to give 113.6 g of product, which was identified by the acronym "C4S-4K-DGBE-TPA". The product exists in the aldehyde and hydrated form and contains residual solvent.

B. Synthesis of the Aldehyde Derivative C4S-4K-DGBE-SBA. C4S-4K-DGBE (10.0 g, 2.5 mmol) was dissolved in 100 mL of water, and the solution pH was adjusted to 9.31 with 1.00 N NaOH. N-Oxysuccinimidyl N-(4-diethoxy)butyrylsuccinamate (4.5 g, 12.5 mmol) in 10 mL DMF was added to the reaction solution. The solution was stirred for 3 hours at room temperature. The solution was reduced in volume under vacuum to about 25 mL. To the solution was added 1 L of ethanol. The slurry was cooled to 5° C. overnight. The solvent was decanted, and the solid was collected by filtration. The solid was washed with ethanol (25 mL) and then ethyl ether (2×25 mL). The solid was dried under vacuum to give 6.8 g of product, which was identified by the acronym "C4S-4K-DGBE-SBDA". A 5.5 g (1.4 mmol) portion of this material was dissolved in 25 mL of water, and the solution pH was adjusted to 1.50 with 1.00 N HCl. The solution was stirred at room temperature for four hours. The volume of solution was reduced to about 10 mL by evaporation under vacuum. Acetone (50 mL) was added. The solvent was decanted, and an additional 50 mL of acetone was added. The solvent was decanted and 50 mL of acetone was added. The mixture was stirred, and the solid was collected by filtration. The solid was dried to give 5.0 g of the desired product. This material was identified by the acronym "C4S-4K-DGBE-SBA".

C. Synthesis of the Maleimide Derivative C4S-4K-DGBE-MP. A solution of C4S-4K-DGBE (7 g, 1.75 mmol) in water (46 mL) and N,N-dimethylformamide (DMF; 23 mL) was added to a stirred solution of N-succinimidyl maleimidopropionate (SMP; 2.78 g, 10.5 mmol) in DMF (140 mL) and water (10 mL) at a rate of 4.5 mL/minute. After the addition was complete, the solution was stirred for an additional one hour. The reaction mixture was evaporated to dryness. The residue was dissolved in water and filtered to removed an insoluble material. The filtrate was diluted with ethanol to precipitate the product (5.83 g), which was identified by the acronym "C4S-4K-DGBE-MP".

D. Synthesis of the Aldehyde Derivative C6S-4K-DGBE-TPA. The pH of a solution of C6S-4K-DGBE (12 g, 3.0 mmol) in water (75 mL) was adjusted to pH 10.0 with 1 N NaOH (43 mL). To this stirred solution was added dropwise a solution of N-succinimidyl 4-thia-7-diethoxy-heptanoate (6.06 g, 18 mmol) in DMF (150 mL). After the addition was completed, the reaction mixture was stirred for three hours at room temperature. Then the solvent was removed by rotary evaporation. Water (100 mL) was added, and the solution was diluted with ethanol (400 mL) to precipitate the product (10 g), an acetal derivative which was identified by the acronym "C6S-4K-DGBE-TPDA". This product was collected by filtration, washed successively with ethanol and ethyl ether and dried under vacuum. Then a 10 g portion was dissolved in 0.1 N HCl (189 mL) to give a solution having a pH of 2.0. The solution was stirred at room temperature for three hours and then evaporated to dryness. The residue was dried under high vacuum at 35° C. to give solidified product (identified by the acronym "C6S-4K-DGBE-TPA; 9.8 g) which existed as a hydrated aldehyde.

E. Synthesis of the Aldehyde Derivative HA-4K-DGBE-TPA. HA-4K-DGBE (6.0 g, 1.5 mmol) was dissolved in 50 mL of water, and the solution pH was adjusted to 9.15 with 5 N NaOH. N-Oxysuccinimidyl 4-thia-7-diethoxyheptanoate (2.7 g, 9 mmol) in N,N-dimethylformamide (20 mL) was added. The solution was stirred for three hours. The solution was evaporated to about 10 mL. Water (20 mL) was added and the solution was evaporated to 10 mL. Ethanol (500 mL) was added and the solution was stirred. The mixture was kept at 5° C. overnight. The solvent was decanted and the solid was collected by filtration. The solid was washed with ethanol (2×25 mL) and then with ethyl ether. The solid was dried under reduced pressure to give 6.6 g of the desired protected aldehyde, which was identified by the acronym "HA-4K-DGBE-TPDA". A 5.0 g portion of said protected aldehyde was dissolved in 35 mL of water. The pH was adjusted to 1.50 with 1.00 N HCl. After about 2.5 hours, the solution was evaporated to about 10 mL. Ethanol (400 mL) was added. The solid was collected and washed with acetone. ($^1$H-NMR indicated that the acetal was not reformed due to the use of ethanol.) The solid was dried under reduced pressure to give 3.6 g of the desired product, which was identified by the acronym "HA-4K-DGBE-TPA".

F. Synthesis of the Aldehyde Derivative C4S-4K-TPA. C4S-4K-NH$_2$ (13.12 g, 3.28 mmol) was dissolved in water (140 mL) to give a solution having a pH of 8.16. The solution pH was adjusted to 9.0 with 1 N NaOH (4.5 mL). To this solution was added a solution of N-succinimidyl-4-thia-7-diethoxyheptanoate (6.62 g, 19.68 mmol) in DMF (140 mL). The reaction mixture was stirred at room temperature for four hours and then evaporated to dryness. The residue was dissolved in water (100 mL) and the solution diluted with ethanol (500 mL) to give an oily product, which was isolated by decantation. Vigorous stirring of the oily product with ethanol gave a solid product (9.3 g), which was isolated by filtration, washed with ethyl ether and dried under high vacuum. This intermediate was identified by the acronym "C4S-4K-TPDA".

C4S-4K-TPDA (8.87 g) was dissolved in water (35 mL) to give a solution having a pH of 4.37. The solution pH was adjusted to 2.0 with 1 N HCl, and the solution was stirred at room temperature. Monitoring the reaction by $^1$H-NMR indicated that the reaction was completed after four hours. The reaction mixture was concentrated under reduced pressure at 35° C. to ¼ of its original volume and diluted with acetone (100 mL) to give an oily product. The latter was isolated by decantation and triturated with acetone to afford a solid product (7.75 g), which was isolated by filtration and dried under high vacuum. NMR data indicated that the product, which was identified by the acronym "C4S-4K-TPA", existed as hydrated aldehyde form.

G. Synthesis of the Aldehyde Reagent C4S-4K-ABA. Chondroitin-4-sulfate (22.2 g, 5.55 mmol) and 4-aminobutyraldehyde diethoxyacetal (7.6 g, 47.0 mmol) were combined in 120 mL of water. The pH was adjusted to 8.35 with 1.00 N HCl. Ethanol (60 mL) was added followed by borane-pyridine complex (5.7 mL). The solution was heated at 40° C. for six days. The solution was cooled and the pH was adjusted to 10.00 with 5.00 N NaOH. To the stirred solution was added 1 L of ethanol. The mixture was stirred for two hours, and the precipitate was collected by filtration. The solid was washed with ethanol (75 mL) followed by ethyl ether (75 mL). The solid was dried under vacuum to give 21.5 g of product, which was identified by the acronym "C4S-4K-ABDA". The product was negative to 2,3,5-triphenyltetrazolium chloride, indicating that coupling between C4S-4K and 4-aminobutyraldehyde diethoxyacetal was successful. C4S-4K-ABDA (6.1 g, 1.5 mmol) was dissolved in 40 mL of water, and the solution pH was adjusted to 1.50 with 1.00 N HCl. After 2.5 hours, the volume of solution was reduced to about 15 mL by evaporation under vacuum. Acetone (150 mL) was added to the solution, and the resulting mixture was stirred for 30 minutes. The solvent was decanted, and an additional 150 mL of acetone was added. The mixture was stirred to give a solid. The solid was collected and dried under reduced pressure to 6.0 g of the desired product, which was identified by the acronym "C4S-4K-ABA".

H. Synthesis of the Aldehyde Reagent HA-4K-TPA. HA-4K-NH$_2$ (9.0 g, 2.25 mmol) was dissolved in 90 mL, of water and the pH was adjusted to 9.15 with 1 N NaOH. N-Oxysuccinimidyl 4-thia-7-diethoxyheptanoate (3.6 g, 11.9 mmol) in DMF (20 mL) was added in one portion. An additional 20 mL of water was added. The solution was stirred for 4.5 hours, and then the volume was reduced to about 25 mL by evaporation under vacuum. Ethanol was added, and the resulting slurry was stirred for two hours. The solid was collected by filtration and was washed with ethanol (25 mL) and then with ethyl ether (25 mL). The solid was dried under reduced pressure to give 9.5 g of product, HA-4K-TPDA. A 9.5 g portion was dissolved in 65 mL of water. The pH was adjusted to 1.50 with 1.00 N HCl. After about 2 hours, the solution was filtered through a 0.2 μm pore-size nylon filter membrane, and the volume of filtrate was reduced by evaporation under vacuum to about 15 mL. Acetone (250 mL) was added, and after 30 minutes the solvent was decanted. An additional 250 mL of acetone was added. The solid was collected and washed acetone (50 mL). The solid was dried under reduced pressure to give 8.9 g of HA-4K-TPA.

I. Synthesis of the Aldehyde Reagent C4S-4K-AOA-DGBE-MP. Both [(t-butyl-oxycarbonyl)amino]oxy]acetic acid and its activated ester derivative N-succinimidyl [[(t-butyloxycarbonyl)amino]oxy]acetate were prepared by known methods. N-Benzyl-oxycarbonyl-N'-[[[(t-Butyloxycarbonyl)amino]oxy]acetyl]-diethylene glycol bis(3-aminopropyl) ether (t-BOC-NHOCH$_2$CO-DGBE-Z) was prepared by the condensation of benzyloxycarbonyl DGBE (17.8 g, 50.4 mmol) with N-succinimidyl [[(t-butyloxycarbonyl)amino]oxy]acetate (13.2 g, 45.8 mmol) in 300 mL of chloroform in the presence of triethylamine (7.0 mL, 50.4 mmol). N-Benzyloxycarbonyl-N'-(aminoxyacetyl)-diethylene glycol bis(3-aminopropyl) ether (H$_2$NOCH$_2$CO-DGBE-Z) was prepared by treatment of t-BOC-NHOCH$_2$CO-DGBE-Z with trifluoroacetic acid in methylene chloride. Both N-succinimidyl 3-maleimidopropionate (SMP) and 3-maleimidopropionic acid were prepared by known methods.

C4S-4K (12.1 g) was dissolved in 40 mL of water, and a solution of H$_2$NOCH$_2$CO-DGBE-Z (17.5 g) in 20 mL of ethanol was added. The solution pH was adjusted to 4.5 (pH strips 0.0–6.0) using 1.00 N NaOH. The solution was heated at 40° C. for two days. The solution was allowed to return to ambient temperature, and the solution pH was adjusted to 10.5 by the addition of sodium hydroxide solution. Ethanol (800 mL) was added to the solution to precipitate the product. The solid was isolated by filtration and washed with ethanol. The solid was air dried to give 16.1 g of product, which was identified by the acronym "C4S-4K-AOA-DGBE-Z".

C4S-4K-AOA-DGBE-Z (5.075 g) was dissolved in 100 mL of water. Pd/C (0.408 g) was added, and the resulting slurry was exposed to hydrogen overnight. The reaction mixture was filtered through a pad of Celite 521, and the filtrate was evaporated to a semi-solid. The semi-solid was dissolved in about 25 mL of water. Ethanol was added to precipitate the product. The product was collected and washed with ethanol and dried under vacuum to give 4.1 g of product, which was identified by the acronym "C4S-4K-AOA-DGBE".

C4S-4K-AOA-DGBE (4.0 g, 1.0 mmol) in 60 mL of water was added dropwise to a solution of N-succinimidyl maleimidopropionate (SMP) in 100 mL of DMF. Water (15 mL) was added to achieve a homogeneous solution. The solution was stirred for one hour and the solvent was evaporated under vacuum. The residue was combined with 40 mL of water and filtered. The filtrate was combined with 600 mL of ethanol. The mixture was left to stand at ambient temperature overnight. The solid was collected and washed with ethanol (2×10 mL). The solid was dried to give 3.5 g of product, which was identified by the acronym "C4S-4K-AOA-DGBE-MP".

EXAMPLE 4. IN VITRO EXPOSURE OF OLGOSACCHARIDE-MODIFIED DIASPIRIN CROSSLINKED DCLHb TO RED CELL PREPARATIONS

Approximately 20 mL of human blood was freshly collected from each of several donors into an evacuated container containing ethylenediaminetetraacetate (EDTA). The blood samples from several donors were pooled in a 50 mL centrifuge tube. One milliliter portions were dispensed into several test tubes. Then a volume of electrolyte diluent (negative control) and a volume of a second test or control solution was added such that the final concentration of the test or control article was that shown in the following table. Another modified hemoglobin which is known to cause red cell aggregation in this test was employed as a positive control. The test tubes were incubated for one hour. A specimen was removed from each test tube, and a slide was prepared from that specimen and stained. Each slide was observed for red cell aggregation and scored on a scale from zero to three, where zero indicated that no aggregation was observed and three indicated that extensive, irreversible aggregation was observed, i.e., disaggregation was not observed following the addition of normal saline solution to the sample.

TABLE 1

Results of in vitro Red Cell Aggregation Testing

| Negative Control Article and Relative Concentration by Volume | Test Article and Relative Concentration by Volume | Extent of Red Cell Aggregation |
|---|---|---|
| 50% Electrolyte Diluent | | No aggregation observed (0) |
| | 10% Positive Control | Few aggregates observed (1) |
| | 30% Positive Control | Many red cell aggregates (1+) |
| | 50% Positive Control | Extensive red cell aggregation and some small platelet clumps observed (2+) |
| | 10% C4S-4K-DCLHb | None seen (0) |
| | 30% C4S-4K-DCLHb | None seen (0) |
| | 50% C4S-4K-DCLHb | None seen (0) |

This test was repeated using each of four C4S-4K-DGBE-TPA-DCLHb test articles having differing extents of hemoglobin modification. In each test, no red cell aggregation was observed in test solutions containing the oligosaccharide reagent-modified hemoglobin. The negative and positive control solutions gave characteristic responses.

What is claimed is:

1. A compound having a formula

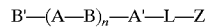

B'—(A—B)$_n$—A'—L—Z wherein

A and B are sugars forming a repeating disaccharide unit in which A and B are joined covalently by a glycosidic bond between C-1 of sugar A and C-3 or C-4 of sugar B, and the repeating disaccharide units are joined covalently to form an oligosaccharide by a glycosidic bond between C-1 of sugar B of a first disaccharide unit and C-3 or C-4 of sugar A in a next successive disaccharide unit, B' is a sugar at a non-reducing terminus of said oligosaccharide of ring structure identical to sugar B, A' is a 1-amino, 1-amido, or 1-imino acyclic hexose joined covalently by a glycosidic bond between C-1 of sugar B at a terminus opposite the non-reducing terminus of said oligosaccharide and C-3 or C-4 of sugar A', n is an integer from 2 to 20, L is an aliphatic, acyclic carbon chain which links Z to the 1-amino, 1-amido or 1-imino group attached to C-1 of sugar A', the aliphatic, acyclic carbon chain containing one or more moieties selected from the group consisting of ether, thio ether, and amide; and Z is at least one electrophilic group.

2. The compound of claim 1, wherein said sugars A and B are selected from the group consisting of N-acetylgalactosamine, N-acetylglucosamine, glucuronic acid, iduronic acid, and glucose.

3. The compound of claim 1, wherein said oligosaccharide is an acid hydrolyzed polysaccharide selected from the group consisting of chondroitin-4-sulfate, chondroitin-6-sulfate, and hyaluronic acid in a molecular size range of 1000–15000 daltons.

4. The compound of claim 1 wherein Z is selected from the group consisting of an aldehyde, an activated ester of a carboxylic acid, a maleimide, an epoxide, a tosyl ester, a tresyl ester, and a halide.

* * * * *